United States Patent [19]
Maguire et al.

[11] Patent Number: 5,778,874
[45] Date of Patent: Jul. 14, 1998

[54] ANESTHESIA MACHINE OUTPUT MONITOR

[75] Inventors: David P. Maguire, Sewell, N.J.; Marc Torjman, Philadelphia, Pa.

[73] Assignee: Thomas Jefferson University, Philadelphia, Pa.

[21] Appl. No.: 725,291

[22] Filed: Oct. 2, 1996

[51] Int. Cl.$^6$ .......................... A61M 16/00; A62B 7/00; A62B 9/00; F16K 31/02
[52] U.S. Cl. .......................... 128/204.22; 128/205.23
[58] Field of Search .................. 128/203.12, 204.21, 128/204.22, 205.23, 716

[56] References Cited

U.S. PATENT DOCUMENTS

| | | | |
|---|---|---|---|
| 3,166,676 | 1/1965 | Robinson | 128/205.23 |
| 4,150,670 | 4/1979 | Jewett et al. | 128/188 |
| 4,215,409 | 7/1980 | Strowe | 128/205.23 |
| 4,241,732 | 12/1980 | Berndtsson | 128/204.21 |
| 4,269,194 | 5/1981 | Rayburn et al. | 128/719 |
| 4,537,190 | 8/1985 | Caillot et al. | 128/204.22 |
| 4,572,208 | 2/1986 | Cutler et al. | 128/718 |
| 4,598,706 | 7/1986 | Darowski et al. | 128/205.23 |
| 4,602,653 | 7/1986 | Ruiz-Vela et al. | 137/88 |
| 4,611,590 | 9/1986 | Ryschka et al. | 128/203.14 |
| 4,627,860 | 12/1986 | Rowland | 55/162 |
| 4,756,670 | 7/1988 | Arai | 417/43 |
| 4,770,168 | 9/1988 | Rusz et al. | 128/203.12 |
| 4,878,388 | 11/1989 | Loughlin et al. | 73/866.4 |
| 4,903,693 | 2/1990 | Yasue | 128/203.12 |
| 4,905,685 | 3/1990 | Olsson et al. | 128/203.12 |
| 4,907,166 | 3/1990 | Corenman et al. | 364/497 |
| 4,986,268 | 1/1991 | Tehrani | 128/204.22 |
| 5,046,018 | 9/1991 | Flewelling et al. | 364/497 |
| 5,049,317 | 9/1991 | Kiske et al. | 261/16 |
| 5,052,382 | 10/1991 | Wainwright | 128/202.25 |
| 5,094,235 | 3/1992 | Westenskow et al. | 128/204.22 |
| 5,231,591 | 7/1993 | Flewelling et al. | 364/497 |
| 5,235,971 | 8/1993 | Falb et al. | 128/203.14 |
| 5,237,990 | 8/1993 | Psaros et al. | 128/204.21 |
| 5,243,973 | 9/1993 | Falb et al. | 128/203.27 |
| 5,253,640 | 10/1993 | Falb et al. | 128/200.24 |
| 5,272,907 | 12/1993 | Hakala | 73/23.2 |
| 5,296,706 | 3/1994 | Braig et al. | 250/339 |
| 5,320,093 | 6/1994 | Raemer | 128/203.12 |
| 5,423,313 | 6/1995 | Olsson et al. | 128/204.21 |
| 5,427,104 | 6/1995 | Briend et al. | 128/654 |
| 5,471,977 | 12/1995 | Olsson et al. | 128/204.22 |

*Primary Examiner*—Kimberly L. Asher
*Attorney, Agent, or Firm*—Woodcock Washburn Kurtz Mackiewicz & Norris LLP

[57] ABSTRACT

An anesthesia machine output monitor (AMOM) which performs the functions of measuring the flow and composition of anesthesia gases delivered by the anesthesia machine, measuring on-line the amount of inhaled anesthetic used during a procedure requiring an anesthetic agent, measuring on-line the cost of inhaled anesthetic used during a procedure requiring an anesthetic agent, and integrating with an automated anesthesia recorder (AAR) to allow the recording of anesthetic gas flow rates and composition during a procedure and the cumulative cost of the anesthetic gases used during the procedure. The anesthesia gas flow rates and composition are measured using a modified infrared anesthetic gas analyzer that measures anesthetic gas composition and a pitot tube that is inserted in the common gas outlet of the anesthesia machine in order to measure the composition and flow rates of gases as they exit the anesthesia machine. Anesthetic gas sampling is accomplished by aspirating anesthetic gases from a sampling port integrated into the pitot tube. The measured gas analog signals are then captured from an I/O port of the capnograph and provided to a processor for on-line processing. An automated anesthesia recorder is preferably provided to permit cost and compliance records to be maintained for each use of the anesthesia machine.

16 Claims, 5 Drawing Sheets

ANESTHESIA MACHINE OUTPUT MONITOR

FIELD OF THE INVENTION

This invention relates to an anesthesia machine output monitor which measures the composition and flow rates of gases delivered by an anesthesia machine from a common gas outlet. The amount of anesthetic agent is monitored to prevent anesthetic overdose and to permit accurate on-line determinations of the cost of the inhalation anesthetic and other gases, such as $O_2$ and $N_2O$, used for each procedure.

BACKGROUND OF THE INVENTION

Numerous devices are known in the prior art which detect the concentration of anesthetic gases in the airstream of a patient under anesthesia. For example, in U.S. Pat. No. 4,150,670, an anesthesia detector is provided in the inspired or expired air pathway of a patient under anesthesia. The measured amounts are fed back to assure that fixed quantities or proportions of anesthetic gas are provided. Information displays and permanent recordings are also provided to permit automatic control of gas flow. However, the disclosed device requires a relatively complicated electromechanical device in which deformation due to directly proportional reversible swelling of an elastic membrane in contact with the gas is mechanically detected and translated into an electrical signal which is used to generate the informational display and/or to provide automatic control of the provision of the anesthetic gas. In addition, no means are provided for measuring the fresh gas output of the anesthesia machine and calculating the volume of anesthesia used by a particular patient so as to provide a cost accounting mechanism for the anesthetic gases, which are typically quite expensive.

Similarly, in U.S. Pat. No. 5,237,990, a sensor is placed between the patient and the vaporizer of the anesthesia device for measuring the concentration of the anesthetic in the patient's respiratory gas. The sensor output is used to control the flow of respiratory gas to the patient so as to compensate for the contribution to the respiratory gas flow of the vaporized anesthetic. However, once again, no means are provided for measuring the fresh gas output of the anesthesia machine and calculating the volume of anesthetics used by a particular patient so as to provide a cost accounting mechanism for the anesthetic gases.

Capnographs and other well-known devices also have been used to monitor the composition of the anesthetic gas mixture breathed by a patient during a procedure requiring anesthesia. For example, the DATEX CAPNOMAC ULTIMA™ pneumatic capnograph uses infrared gas capnography to monitor the composition of the anesthetic gas mixture breathed by a patient during a procedure requiring anesthesia and uses a pitot tube to measure respiratory gas flow rates with each breath. The DATEX CAPNOMAC ULTIMA™ pneumatic capnograph is designed to be connected to an endotracheal tube in order to measure inspiratory and expiratory anesthetic gas composition and gas flow rates. However, as with the other prior art devices, the DATEX CAPNOMAC ULTIMA™ pneumatic capnograph does not measure the fresh gas output of the anesthesia machine and provide a cost accounting mechanism for the anesthetic gases.

It is, accordingly, a primary object of the present invention to measure directly, and on-line, the fresh gas output of an anesthesia machine and to monitor the amount of inhalation anesthetic used during a procedure requiring use of anesthesia.

It is a further object of the present invention to provide automated on-line record keeping of anesthetic gas flow rates and anesthetic agent composition and the cumulative total anesthetic cost during a procedure requiring anesthesia.

It is also an object of the present invention to prevent anesthetic agent overdose and to assure compliance with guidelines on the use of specific anesthetic agents.

SUMMARY OF THE INVENTION

The above and other objects have been met in accordance with the present invention by providing an anesthesia machine output monitor (AMOM) which performs the functions of measuring the flow and composition of anesthesia gases delivered by an anesthesia machine, measuring on-line the amount of inhaled anesthetic used during a procedure requiring an anesthetic agent, measuring on-line the cost of inhaled anesthetic used during a procedure requiring an anesthetic agent, and integrating with an automated anesthesia recorder (AAR) to allow the recording of anesthetic gas flow rates and gas composition during a procedure and the cumulative cost of the procedure.

An anesthesia machine with an output monitor in accordance with the invention includes a computerized data processing system designed to measure the composition and flow rates of gases delivered by the anesthesia machine. In a preferred embodiment of the invention, anesthesia gas flow rates and composition are measured using a modified DATEX CAPNOMAC ULTIMA™ pneumatic capnograph which, as noted above, consists of an infrared anesthetic gas analyzer that measures anesthetic gas composition and a pitot tube that measures gas flow rates. Since the monitor in accordance with the invention is designed to measure the fresh gas output of the anesthesia machine, the DATEX CAPNOMAC ULTIMA™ pitot tube is inserted in the common gas outlet of the anesthesia machine in order to measure the composition and flow rates of gases as they exit the anesthesia machine. Anesthetic gas sampling is accomplished by aspirating anesthetic gases from a sampling port integrated into the DATEX CAPNOMAC ULTIMA™ pitot tube. The measured gas analog signals are then captured from the I/O port of the DATEX CAPNOMAC ULTIMA™ pneumatic capnograph, converted into ASCII data bits by an A/D converter, and provided to a processor for on-line processing.

The anesthesia machine fresh gas flow rates are measured by the pitot tube. For use in the invention, the pitot tube is modified in two ways. First, since the pitot tube used with the DATEX CAPNOMAC ULTIMA™ pneumatic capnograph is designed to measure the flow of respiratory gases during both inspiration and exhalation, the pitot tube is positioned to measure gas flow in one direction only. Second, an insert is placed into the narrow extremity of the pitot tube to increase the resistance to gas flow through it thereby increasing the voltage sensitivity of the pitot tube at lower gas flow rates. This modification is necessary due to the insensitivity of the DATEX CAPNOMAC ULTIMA™ pitot tube differential pressure transducer at low flow rates.

The gas flow and gas composition data provided to the processor is then processed to allow display of a CRT of the following information: total gas flow (L/min), percent concentration of each gas and the inhalation anesthetic agent (volume percent), and the cost of inhaled anesthetic and other gases ($O_2$ and $N_2O$) used in dollars. In addition, if an automated anesthesia recorder is used, anesthetic gas flow and composition data as well as cumulative cost information can be sent to the automated anesthesia recorder for charting. The resulting records can then be used to permit cost recovery and to verify that guidelines applicable to the use of the anesthetic agents have been followed.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 1-4. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

Figure 1:
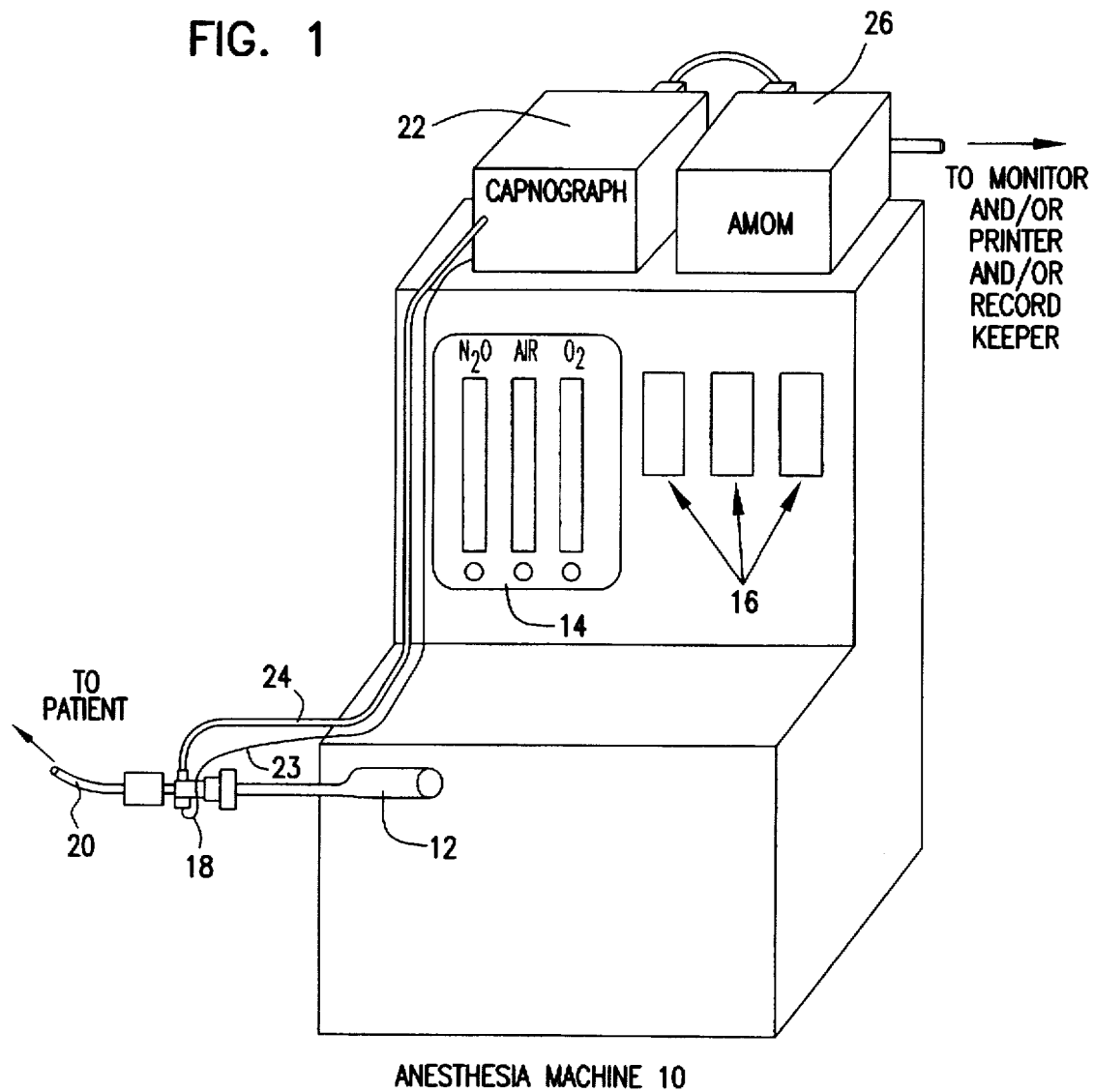
FIG. 1 is an illustration of an anesthesia machine modified to embody the present invention.

An anesthesia machine 10 with an output monitor in accordance with the invention is illustrated generally in FIG. 1. As illustrated in FIG. 1, the anesthesia machine 10 provides anesthetic carrier gases such as $N_2O$, air, and $O_2$ via a common gas outlet 12 to a patient during a procedure requiring general anesthesia. As desired, the monitoring technique of the invention may also be used to monitor patient ventilation using regular air. The gases available for use by the operator, and the quantities thereof, are displayed on gauges 14, and the selected carrier gas or gases are passed through vaporizers 16 in order to deliver the selected potent inhalation anesthetic to the common gas outlet 12. In accordance with the invention, the anesthesia machine 10 so configured is modified to include an anesthesia machine output gas monitoring system comprising a pitot tube 18 placed in the output line 20 to the patient, a capnograph 22 connected to the output of the pitot tube 18 via electrical line 23 and air line 24, and an anesthesia machine output monitor (AMOM) 26. As will be described in more detail below with respect to FIGS. 2-4, the data processing system of AMOM 26 is designed to measure the composition and flow rates of gases delivered by the anesthesia machine 10 and the costs of the provided gas mixture in real-time.

In a preferred embodiment of the invention, the anesthesia gas flow rates and composition are measured using a modified DATEX CAPNOMAC ULTIMA™ pneumatic capnograph 22 consisting of an infrared anesthetic gas analyzer that measures anesthetic gas composition and a pitot tube 18 that measures gas flow rates. Since the present invention is designed to measure the fresh gas output of the anesthesia machine 10, the DATEX CAPNOMAC ULTIMA™ pitot tube is inserted in the common gas outlet 12 of the anesthesia machine 10 in order to measure the composition and flow rates of gases as they exit the anesthesia machine 10.

As known to those skilled in the art, a pitot tube such as the one used in the DATEX CAPNOMAC ULTIMA™ pneumatic capnograph system generally consists of a straight tube which is placed vertically in the moving gas and is fitted with an elbow connector such that the mouth of the bent part is directed upstream. Typically, the pitot tube is used with a manometer to measure the velocity of gas flow through the pitot tube. In accordance with the invention, the anesthesia machine fresh gas flow rates are to be measured by the pitot tube. Accordingly, the pitot tube 18 is modified in two ways. First, since the pitot tube used with the DATEX CAPNOMAC ULTIMA™ pneumatic capnograph is designed to measure the flow of respiratory gases during both inspiration and exhalation, the pitot tube is adapted to measure gas flow in one direction only. Second, an internal reducer 38 (FIG. 3) or an insert is placed into the narrow extremity of the pitot tube 18 to increase the resistance to gas flow through it thereby increasing the voltage sensitivity of the pitot tube 18 at lower gas flow rates. This modification is necessary due to the insensitivity of the DATEX CAPNOMAC ULTIMA™ pitot tube differential pressure transducer at low flow rates.

Figure 2A:
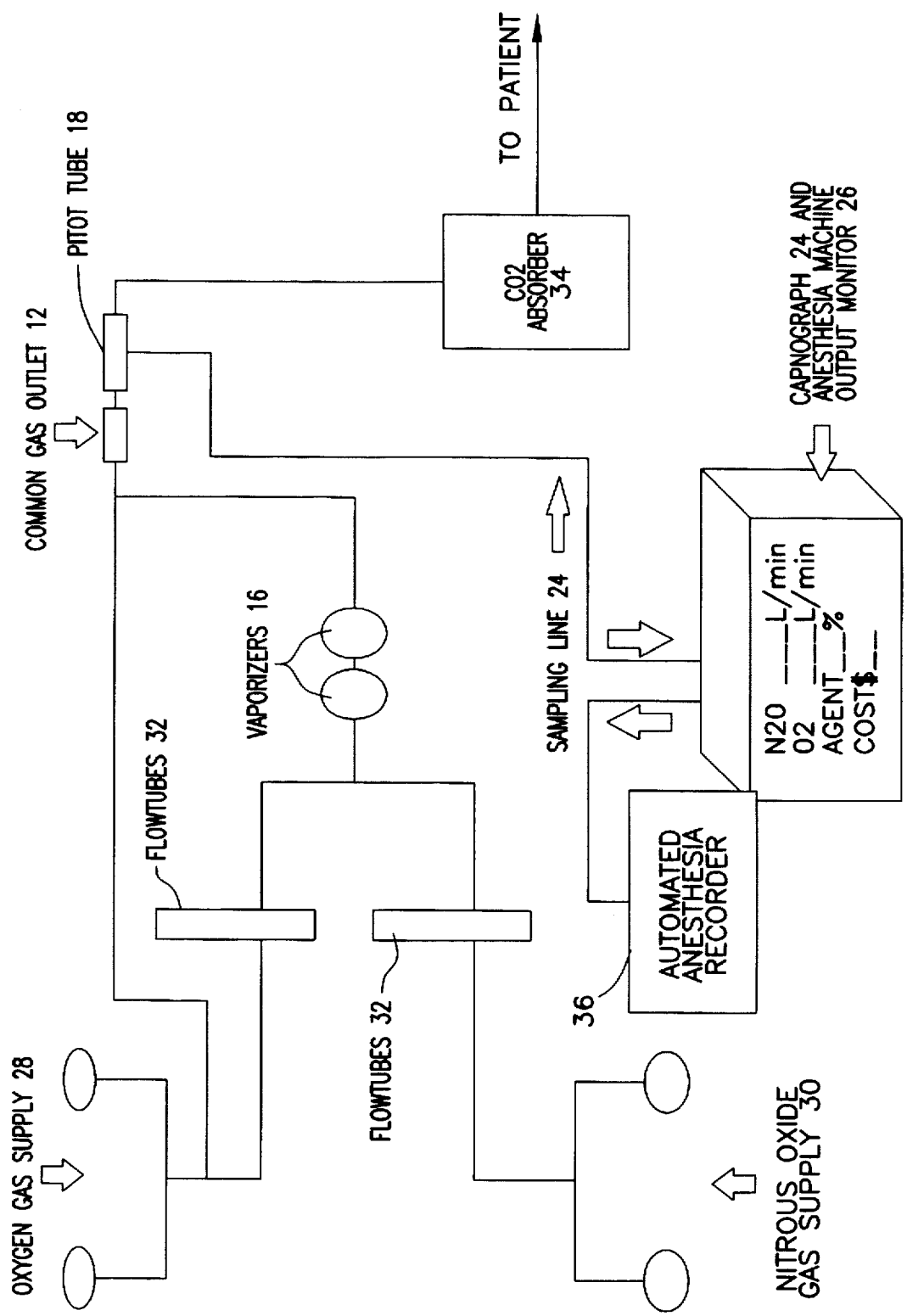
FIG. 2A is a functional diagram illustrating the operation of a preferred embodiment of the anesthesia machine of FIG. 1.

FIG. 2A is a functional diagram illustrating the operation of the anesthesia machine of FIG. 1. As illustrated, oxygen from an oxygen gas supply 28 and/or an anesthetic agent gas such as nitrous oxide from a nitrous oxide gas supply 30 are provided to the common gas outlet 12. The oxygen may be provided directly to the common gas outlet 12 or can be provided via flow tubes 32 for mixing with the anesthetic agent gas. The mixed gas is typically passed through vaporizers 16 in order to add the potent anesthetic agent gases to the mixed gas prior to common gas outlet 12. As shown, the pitot tube 18 is typically connected to the output side of the common gas outlet 12; however, in the alternative embodiment of FIG. 2B, the pitot tube 18' may be connected between the vaporizers 16 and the common gas outlet 12. Of course, this latter embodiment may require access to the internal structure of the anesthesia machine 10. The output gas mixture from the pitot tube 18 or 18' is then provided to the anesthesia monitoring device of the invention before the output gas is provided to the patient. A $CO_2$ absorber 34 may also be provided for removing the $CO_2$ from the output gas.

The anesthetic gas sampling in accordance with the invention is preferably accomplished by aspirating anesthetic gases from a sampling port integrated into the DATEX CAPNOMAC ULTIMA™ pitot tube 18 or 18'. The measured gas analog signals are provided via sampling line 24 to the capnograph 24 and the AMOM 26 for calculation of the flow rates, agent composition, and cumulative costs in accordance with the techniques of the invention. The results of the calculation are then stored in the automated anesthesia recorder (AAR) 36 for maintaining cost records and records of compliance with guidelines on the use of anesthetic agents provided by the anesthesia machine 10.

Figure 3:
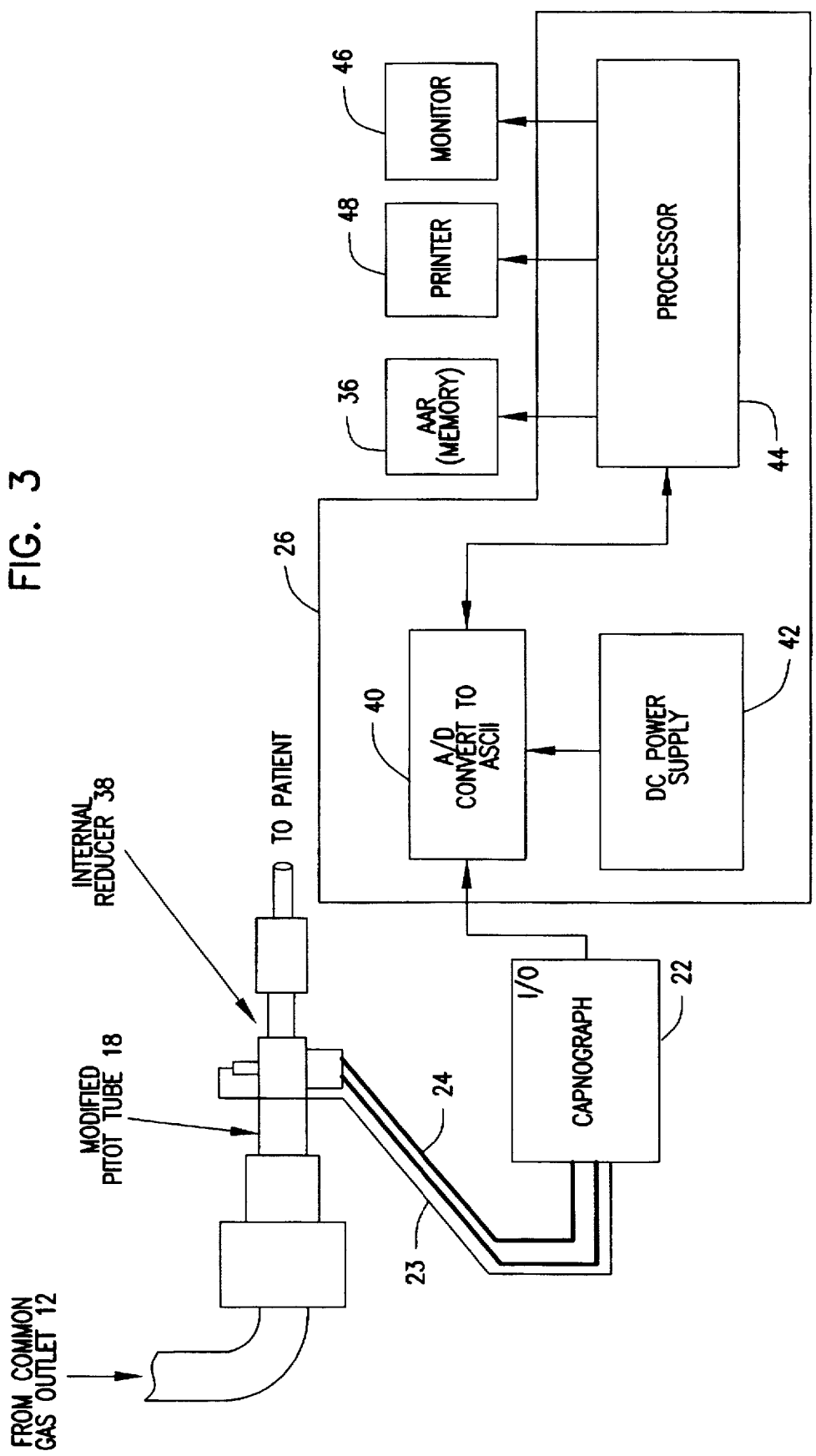
FIG. 3 illustrates in more detail the pitot tube and the anesthesia machine output monitor of the anesthesia machine of FIG. 1.

FIG. 3 illustrates in more detail the pitot tube 18 and the anesthesia machine output monitor 26 used with the anesthesia machine 10 of FIG. 1. As illustrated, the pitot tube 18 is preferably connected to the output side of the common gas outlet 12 to permit sampling of the anesthesia machine's output. As noted above, the pitot tube 18 is a modified version of the pitot tube typically used with the DATEX CAPNOMAC ULTIMA™ pneumatic capnograph to measure the flow of respiratory gases during both inspiration and exhalation. The pitot tube 18 of the invention is adapted to measure gas flow in one direction only and further includes an internal reducer 38 or an insert (e.g., 21 mm×8 mm inner diameter×13 mm outer diameter) which is placed into the narrow extremity of the pitot tube 18 to increase the resistance to gas flow through it, thereby increasing the voltage sensitivity of the pitot tube 18 at lower gas flow rates. As noted above, this modification is necessary due to the insensitivity of the DATEX CAPNOMAC ULTIMA™ pitot tube differential pressure transducer at low flow rates.

The gas samples from the pitot tube 18 are then provided via path 24 to a capnograph 22 such as the DATEX CAPNOMAC ULTIMA™ pneumatic capnograph described above. Also, an anesthetic agent gas type detector situated at the pitot tube 18 may provide an input to the capnograph 22 via signal path 23 for processing. Gas analog signals are then captured from the serial and analog I/O port of the DATEX CAPNOMAC ULTIMA™ pneumatic capnograph and converted into ASCII data bits by an A/D converter 40, which is preferably provided as a bus module powered by an optional 10 Volt DC power supply 42. The gas voltage signal is then received by processor 44 for on-line processing. Processor 44 may be, for example, an IBM compatible PC.

The gas flow and gas composition data provided to the processor is processed to allow display on a monitor 46 or printing by a printer 48 of at least the following information: total gas flow for each anesthetic agent (L/min), percent concentration of each inhalation anesthetic agent (volume percent), and the cost of inhaled anesthetic used in dollars. In addition, if an automated anesthesia recorder 36 is used, anesthetic gas flow and composition data as well as cumulative cost information can be sent to the automated anesthesia recorder 36 for charting.

Figure 4:
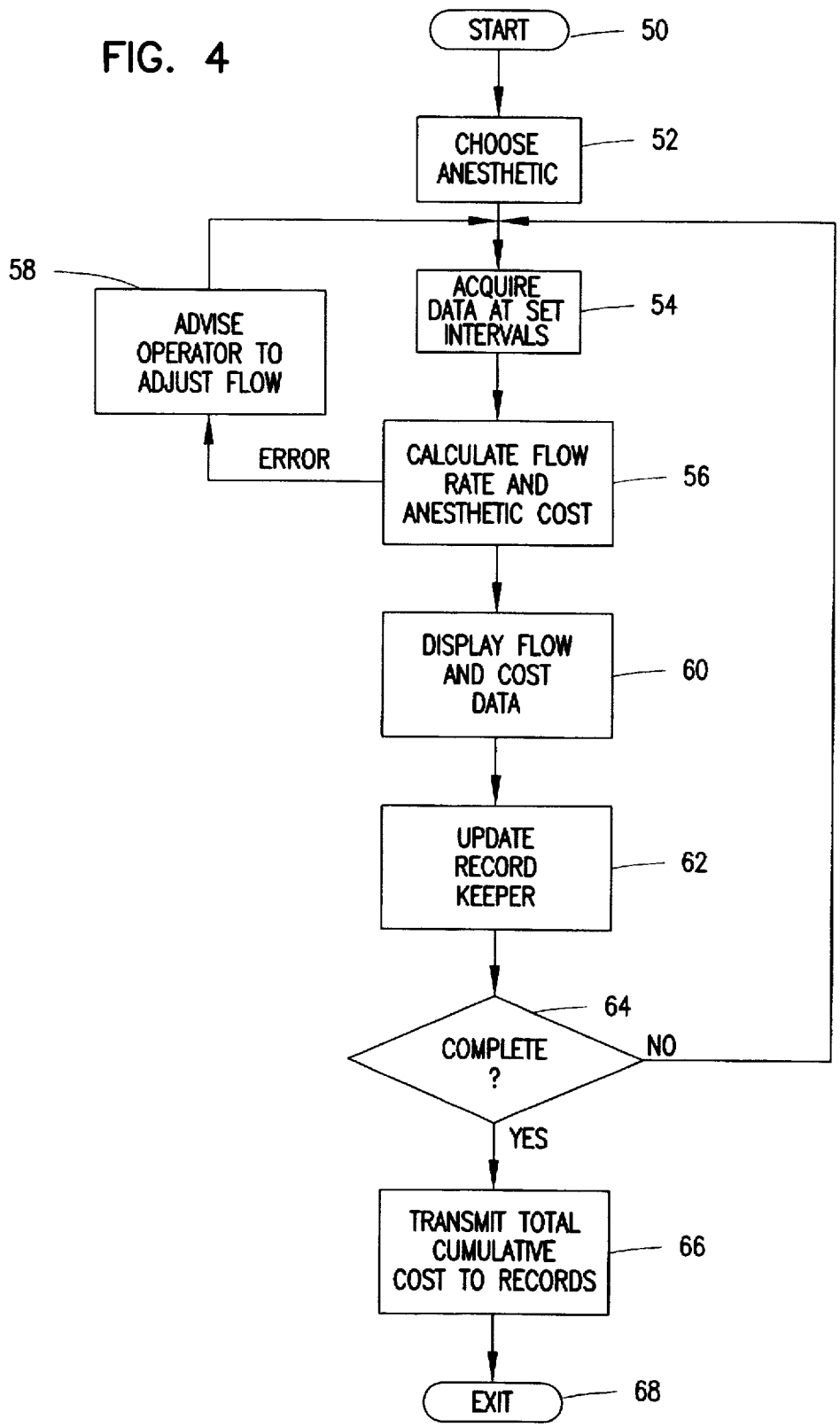
FIG. 4 is a flow chart representing the operation of the invention during a typical patient procedure requiring anesthesia.

FIG. 4 is a flow chart representing the operation of the invention during a typical patient procedure requiring anesthesia. In a preferred embodiment, the flow chart of FIG. 4 is implemented as a software program on processor 44. Preferably, the gas flow and gas composition data provided to the processor 44 is processed in accordance with the routine of FIG. 4 to allow display on a monitor 46 or printing by a printer 48 of at least the total gas flow (L/min.), the percent of nitrous oxide, the percent oxygen, the percent anesthetic agent, the inhalation anesthetic concentration (volume percent), and the cost of the inhaled anesthetic used in dollars. In addition, messages may be displayed to the operator when software of the processor 44 determines that the flow rates are outside of (exceed) default limits so that the operator knows to adjust (decrease) the gas flow rate.

The routine of FIG. 4 starts at step 50 by turning on the anesthesia machine output monitor 26, booting-up the processor 44, monitoring internal calibration, and zeroing readings as necessary. Then, in step 52 a main menu is displayed on monitor 46 to permit the operator to choose the anesthetic gas to be monitored. The molecular weight of the selected anesthetic gas is also entered into Equation 3 below. Next, the fresh gas flow limits are displayed to the operator, and the limits for the fresh gas flow rates are preset to the appropriate user guidelines or preferences. Data collection then begins at step 54. Digital signals from the DATEX CAPNOMAC ULTIMA™ pneumatic capnograph 22 measuring the total gas flow ($v_b$), the percent nitrous oxide (%N2O), the percent oxygen (%O2), and the percent inhaled anesthetic (D) are then acquired at predetermined intervals, such as every 6 seconds.

At step 56, the flow rates and anesthetic costs are calculated and shown on monitor 46 at the predetermined intervals (e.g., every 6 seconds). In particular, processor 44 converts the flow data recorded in millivolts to liters per minute using a calibration table. Then, the flow rate of nitrous oxide ($N2O_f$) in liters per minute is calculated as follows:

$$N2O_f = (V_b)\,(\%N2O)\,(0.01) \qquad \text{Equation 1}$$

and the flow rate of oxygen ($O2_f$) in liters per minute is calculated as follows:

$$O2_f = (V_b)\,(\%O2)\,(0.01) \qquad \text{Equation 2}$$

Next, the cumulative cost of the inhaled anesthetic is calculated by adding to the previous cumulative cost the cost of the anesthetic for the current 6 second interval, calculated as follows:

$$P_i = (P_g)(0.1)(V_b)(D/100)(MW/22.4)(273/293)[(100-D)/(100-D)]\ \text{Equation 3}$$

where:
  $P_i$=cost of anesthetic for the current 6 second interval;
  $P_g$=cost of anesthetic per gram;
  $V_b$=total gas flow;
  D=inhaled anesthetic concentration; and
  MW=inhaled anesthetic molecular weight.

If the flow rates determined at step 56 are found to exceed default limits or to otherwise fall outside the acceptable ranges, a visual and/or auditory signal is activated at step 58 to advise the operator to decrease or otherwise adjust the fresh gas flow rate. Data collection at step 54 then resumes.

The current flow rate for nitrous oxide and oxygen, the inhaled anesthetic concentration, and preferably the cost data are displayed to the operator on the monitor 46 at step 60. If an automated anesthesia recorder (AAR) 36 is provided, the recorded data is also sent to the AAR at step 62 at regular intervals, such as every 5 minutes. The AAR 36 also may be updated when a change in flow rate and/or anesthetic concentration is detected.

If it is determined at step 64 that the provision of anesthetic gases is complete (i.e., the operator closes the anesthesia supply or presses an <end> key), an end of record marker is entered and the total cumulative cost data for the inhaled anesthetic is transmitted to the AAR 36 at step 66. The routine is then exited at step 68. On the other hand, if it is determined at step 64 that the operator has not concluded the provision of anesthetic gases, additional data is collected at step 54 and the process is repeated.

Preliminary data from the monitoring of several different anesthesia machines using the anesthesia machine output monitoring system of the invention shows that there is some variability between anesthesia machines in the flow calibration curve. To overcome this problem, those skilled in the art will appreciate that each anesthesia machine output monitor 26 may be readily calibrated to the characteristics of the particular anesthesia machine 10 with which it is used.

Also, those skilled in the art will appreciate that back pressure generated from an anesthesia ventilator may affect the flow measurements. In such a case, the software routine of FIG. 4 may be modified to eliminate the resulting artifacts in the measured data. In addition, a mushroom valve (not shown) may be placed downstream after the pitot tube 18 or 18' to prevent gases present in the anesthesia circuit from flowing back into the gas sensor via the sample line 24 during positive pressure ventilation. A pressure gauge between the mushroom valve and the pitot tube 18 or 18' also may be used to monitor any malfunction of the mushroom valve.

As described herein, the present invention provides a straight-forward technique for automatically capturing information about anesthesia gas flows and compositions output by an anesthesia machine, independent of the patient's respiratory operation. Those skilled in the art will appreciate that the monitoring device of the invention can easily be integrated into existing automatic anesthesia systems to allow the capture of this information as well as cost data for purposes of patient/insurance reimbursement. Also, the monitoring device of the invention permits the anesthetic gas concentration to be monitored in order to guard against anesthetic overdoses, while also assuring compliance with governmental and departmental guidelines on the use of anesthetic agents on patients. Those skilled in the art will also appreciate that the invention may be used for all patients undergoing general anesthesia from pediatric to geriatric populations.

It will be appreciated by those skilled in the art that the foregoing has set forth the presently preferred embodiment of the invention and an illustrative embodiment of the invention but that numerous alternative embodiments are possible without departing from the novel teachings of the invention. For example, the use of a pneumatach flow turbine or other flow measuring device may be substituted for the pitot tube 18 since these devices can also measure flow accurately. Accordingly, all such modifications are intended to be included within the scope of the appended claims.

We claim:

1. A device for measuring anesthetic gas concentration delivered to a patient during a medical procedure requiring an anesthetic gas, comprising:

a supply which provides an anesthetic gas to a patient during a medical procedure;

a capnograph which determines flow rates and concentrations of respective gases input thereto;

a gas sampling device which provides a sample of gas output from said supply to said capnograph;

a processor which processes the flow rates and concentrations of gases in said sample provided to said capnograph by said gas sampling device to determine a cumulative cost of at least anesthetic gas used during said medical procedure; and a display which displays at least said flow rates and gas concentrations of said sample to an operator of said device.

2. A device as in claim 1, further comprising a gas outlet on said device, wherein said gas sampling device is connected to an output of said gas outlet.

3. A device as in claim 1, further comprising a gas outlet on said device, wherein said gas sampling device is connected between said supply and said gas outlet.

4. A device as in claim 1, wherein said gas sampling device comprises a pitot tube with a narrow internal diameter, said pitot tube being sensitive to gas flow in one direction.

5. A device as in claim 1, wherein said capnograph has an I/O port for providing said flow rates and concentrations of gases in said sample to said processor.

6. A device as in claim 1, further comprising a data recorder connected to an output of said processor, said data recorder recording anesthetic gas flow rates, gas concentrations, and said cumulative cost of at least anesthetic gas used during said medical procedure.

7. A device as in claim 1, wherein said display further displays said cumulative cost determined by said processor.

8. A device as in claim 1, wherein said processor displays a message on said display instructing said operator to adjust a flow rate of anesthetic gas when said processor determines that at least one of said flow rates and said concentrations is out of an acceptable range.

9. A device as in claim 1, wherein said gas sampling device comprises a pneumatach flow turbine.

10. A method of providing anesthetic gases from an anesthetic gas supply in prescribed concentrations to a patient during a medical procedure requiring an anesthetic gas, comprising the steps of:

selecting at least one anesthetic gas to be provided to a patient during a medical procedure;

sampling gases provided from said gas supply during said medical procedure at a point between said gas supply and the patient;

determining flow rates and concentrations of said sampled gases;

determining a cumulative cost of anesthetic gases used during said medical procedure; and displaying at least said flow rates and gas concentrations of said sampled gases to an operator.

11. A method as in claim 10, wherein gases from said gas supply are sampled in said sampling step at an output of a gas outlet of said gas supply.

12. A method as in claim 10, wherein gases from said gas supply are sampled in said sampling step at a point between said gas supply and a gas outlet of an anesthesia machine associated with said gas supply.

13. A method as in claim 10, wherein said sampling step comprises the step of reducing a diameter of an output tube of said gas supply as gas output from said gas supply passes through a pitot tube, thereby increasing sensitivity of said pitot tube to gas flow therethrough.

14. A method as in claim 10, comprising the further step of recording anesthetic gas flow rates, gas concentrations, and said cumulative cost of anesthetic gases used during said medical procedure.

15. A method as in claim 10, wherein said displaying step comprises the step of displaying said cumulative cost determined by said processor to said operator.

16. A method as in claim 10, comprising the further step of displaying a message on said display instructing the operator to adjust a flow rate of anesthetic gases when it is determined in said flow rates and concentrations determining step that at least one of said flow rates and said concentrations is out of an acceptable range.

* * * * *

UNITED STATES PATENT AND TRADEMARK OFFICE
CERTIFICATE OF CORRECTION

Figure 2B:
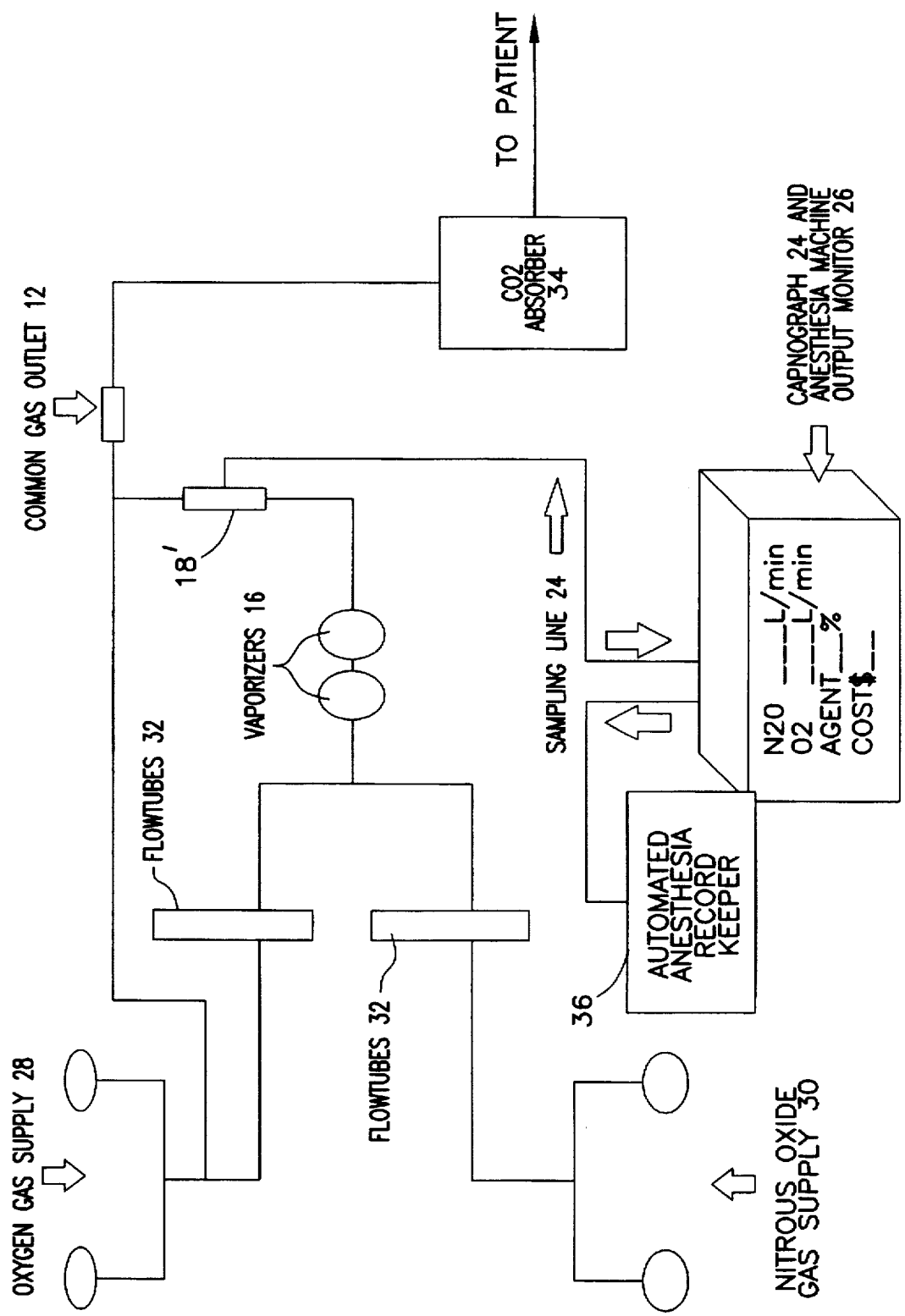
FIG. 2B is a functional diagram illustrating the operation of an alternative embodiment of the anesthesia machine of FIG. 1.

PATENT NO. : 5,778,874
DATED : July 14, 1998
INVENTOR(S) : David P. Maguire and Marc Torjman It is certified that error appears in the above-identified patent and that said Letters Patent is hereby corrected as shown below:

Column 4, line 42, change "this latter" to --the embodiment of Figure 2B--.

Column 6, line 16, in Equation 3, the equation is not legible since the words "Equation 3" are going through the equation.

The Equation should read as follows:

$$P_i=(P_g)(0.1)(V_b)(D/100)(MW/22.4)(273/293[(100-D)/(D/100)]$$

Equation 3

Signed and Sealed this

Thirteenth Day of October 1998

Attest:

BRUCE LEHMAN

*Attesting Officer*            *Commissioner of Patents and Trademarks*